US009440088B2

(12) United States Patent
Perschbacher et al.

(10) Patent No.: US 9,440,088 B2
(45) Date of Patent: Sep. 13, 2016

(54) IMPLANTED LEAD ANALYSIS SYSTEM AND METHOD

(71) Applicant: Cardiac Pacemakers, Inc., St. Paul, MN (US)

(72) Inventors: David L. Perschbacher, Coon Rapids, MN (US); Deepa Mahajan, Roseville, MN (US); Arjun D. Sharma, St. Paul, MN (US); Jeffry V. Marshik, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 165 days.

(21) Appl. No.: 14/099,381

(22) Filed: Dec. 6, 2013

(65) Prior Publication Data

US 2014/0163629 A1 Jun. 12, 2014

Related U.S. Application Data

(60) Provisional application No. 61/734,198, filed on Dec. 6, 2012.

(51) Int. Cl.
*A61N 1/372* (2006.01)
*A61N 1/39* (2006.01)
*A61N 1/362* (2006.01)
*A61N 1/37* (2006.01)

(52) U.S. Cl.
CPC .......... *A61N 1/3962* (2013.01); *A61N 1/3621* (2013.01); *A61N 1/3706* (2013.01); *A61N 1/37247* (2013.01)

(58) Field of Classification Search
CPC .............. A61N 1/3962; A61N 1/3706; A61N 1/3621; A61N 1/37247; A61N 2001/083
See application file for complete search history.

(56) References Cited

U.S. PATENT DOCUMENTS

| 4,562,841 A | 1/1986 | Brockway et al. |
| 4,969,464 A | 11/1990 | Callaghan et al. |
| 5,443,485 A | 8/1995 | Housworth et al. |

(Continued)

FOREIGN PATENT DOCUMENTS

| WO | 2005018738 | 3/2005 |
| WO | 2012166901 | 12/2012 |
| WO | 2016019048 | 2/2016 |

OTHER PUBLICATIONS

Clarke, Malcolm et al., "Automatic adjustment of pacemaker stimulation output correlated with continuously monitored capture thresholds: a multicenter study," European Microny Study Group. Packing Clin. Electrophysiol. Aug. 1998, 21:1567-75.

(Continued)

*Primary Examiner* — Mark W Bockelman
(74) *Attorney, Agent, or Firm* — Pauly, DeVries Smith & Deffner, LLC

(57) ABSTRACT

The technology disclosed herein relates to a method for lead analysis for an implanted medical device. A summary data record is retrieved associated with one or more episodes from an implanted medical device through a communication module. Episode selection criteria are applied to the summary data record by a processing module. One or more episode data records are retrieved from the implanted medical device for one or more episodes for which the episode selection criteria was satisfied. Noise detection criteria are applied to the episode data record. A notification module is configured to generate an alert if the noise detection criteria are satisfied.

20 Claims, 12 Drawing Sheets

(56) References Cited

U.S. PATENT DOCUMENTS

| | | | |
|---|---|---|---|
| 5,690,685 | A | 11/1997 | Kroll et al. |
| 5,814,088 | A | 9/1998 | Paul et al. |
| 6,041,250 | A | 3/2000 | Depinto et al. |
| 6,112,119 | A | 8/2000 | Schuelke et al. |
| 6,263,238 | B1 | 7/2001 | Brewer et al. |
| 6,505,071 | B1 | 1/2003 | Zhu et al. |
| 6,609,023 | B1 | 8/2003 | Fischell et al. |
| 6,721,600 | B2 | 4/2004 | Jorgenson et al. |
| 6,917,830 | B2 | 7/2005 | Palreddy et al. |
| 6,978,182 | B2 | 12/2005 | Mazar et al. |
| 7,047,083 | B2 | 5/2006 | Gunderson et al. |
| 7,155,275 | B2 | 12/2006 | Linder et al. |
| 7,215,993 | B2 | 5/2007 | Lin |
| 7,283,863 | B2 | 10/2007 | Gunderson et al. |
| 7,289,851 | B2 | 10/2007 | Gunderson et al. |
| 7,647,185 | B2 | 1/2010 | Tarassenko et al. |
| 7,894,886 | B2 | 2/2011 | Ghanem et al. |
| 7,974,690 | B2 | 7/2011 | Kracker |
| 7,991,472 | B2 | 8/2011 | Levine et al. |
| 7,991,492 | B1 | 8/2011 | Namanny et al. |
| 8,099,166 | B2 | 1/2012 | Schüller et al. |
| 8,249,709 | B2 | 8/2012 | Davenport et al. |
| 8,260,419 | B2 | 9/2012 | Gunderson |
| 8,483,813 | B2 * | 7/2013 | Zhang .................. A61B 5/0464 600/515 |
| 8,626,293 | B2 | 1/2014 | Bornzin et al. |
| 8,942,791 | B2 | 1/2015 | Dong et al. |
| 2003/0187337 | A1 | 10/2003 | Tarassenko et al. |
| 2003/0204215 | A1 | 10/2003 | Gunderson et al. |
| 2004/0260350 | A1 | 12/2004 | Brandstetter et al. |
| 2005/0192504 | A1 | 9/2005 | Palreddy et al. |
| 2006/0085038 | A1 | 4/2006 | Linder et al. |
| 2006/0247695 | A1 | 11/2006 | Stalsberg et al. |
| 2006/0253164 | A1 | 11/2006 | Zhang et al. |
| 2007/0016261 | A1 | 1/2007 | Dong et al. |
| 2007/0129762 | A1 | 6/2007 | Worley |
| 2007/0219453 | A1 | 9/2007 | Kremliovsky et al. |
| 2008/0161870 | A1 | 7/2008 | Gunderson et al. |
| 2008/0275519 | A1 | 11/2008 | Ghanem et al. |
| 2010/0147983 | A1 | 6/2010 | Evans |
| 2010/0204745 | A1 | 8/2010 | Li et al. |
| 2010/0312131 | A1 | 12/2010 | Naware et al. |
| 2010/0318151 | A1 | 12/2010 | Saha et al. |
| 2011/0077541 | A1 | 3/2011 | Dong et al. |
| 2011/0106191 | A1 | 5/2011 | Bennett et al. |
| 2012/0158089 | A1 | 6/2012 | Bocek et al. |
| 2012/0203123 | A1 | 8/2012 | Mahajan et al. |
| 2012/0271185 | A1 | 10/2012 | Sanghera et al. |
| 2013/0138004 | A1 | 5/2013 | Dong et al. |
| 2013/0138005 | A1 | 5/2013 | Dong et al. |
| 2016/0030752 | A1 | 2/2016 | Mahajan et al. |

OTHER PUBLICATIONS

"Communication Pursuant to Rules 161(1) and 162 EPC," for European Patent Application No. 12731213.0, mailed Jan. 24, 2014 (2 pages).
"Final Office Action," for U.S. Appl. No. 12/815,871, mailed Apr. 14, 2014 (17 pages).
"Final Office Action Response," for U.S. Appl. No. 12/815,871, filed Jul. 14, 2014 (12 pages).
"Final Office Action," for U.S. Appl. No. 12/815,871, mailed Feb. 20, 2015 (20 pages).
"Final Office Action Response," for U.S. Appl. No. 12/815,871, filed with the USPTO Jun. 11, 2015 (13 pages).
"Final Office Action," mailed Dec. 31, 2012 in co-pending U.S. Appl. No. 12/815,871, (14 pages).
"Final Office Action Response," filed Mar. 28, 2013 in co-pending U.S. Appl. No. 12/815,871, (10 pages).
"International Preliminary Report on Patentability," for PCT/US2012/040186, mailed Dec. 12, 2013 (8 pages).
"International Preliminary Report on Patentability," from International Application No. PCT/US2010/038665, corresponding to U.S. Appl. No. 61/187,096, mailed Dec. 29, 2011, pp. 1-8, 8.
"International Search Report and Written Opinion," for PCT/US2015/042711 mailed Oct. 19, 2015 (12 pages).
Kam, Ruth "Automatic Capture Verification in Pacemakers (Autocapture)—Utility and Problems," Indian Pacing and Electrophysiology Journal 2004, 4(2):73-78.
"Non-Final Office Action," for JP Application No. 2012-516200, mailed May 15, 2014 (7 pages).
"Non-Final Office Action," for U.S. Appl. No. 13/483,394, mailed May 21, 2014 (10 pages).
"Non-Final Office Action Response," for U.S. Appl. No. 13/483,394, filed Aug. 15, 2014 (11 pages).
"Non-Final Office Action," for U.S. Appl. No. 12/815,871, mailed Aug. 1, 2014 (20 pages).
"Non-Final Office Action Response," for U.S. Appl. No. 12/815,871, filed Dec. 16, 2014 (14 pages).
"Non-Final Office Action," for U.S. Appl. No. 12/815,871, mailed Nov. 8, 2013 (17 pages).
"Non-Final Office Action Response," for U.S. Appl. No. 12/815,871, filed Feb. 7, 2014 (11 pages).
"Non-Final Office Action," for U.S. Appl. No. 13/483,387, mailed May 15, 2014 (13 pages).
"Non-Final Office Action Response," for U.S. Appl. No. 13/483,387, filed Aug. 15, 2014 (12 pages).
"Non-Final Office Action," mailed Jul. 18, 2012 in U.S. Appl. No. 12/815,871, (15 pages).
"Non-Final Office Action Response," filed Oct. 18, 2012 in U.S. Appl. No. 12/815,871, (12 pages).
"Office Action," from JP Application No. 2012-516200, mailed Oct. 16, 2013 (6 pages).
"PCT International Search Report and Written Opinion," from International Application No. PCT/US2010/038665, corresponding to U.S. Appl. No. 12/815,871, mailed Sep. 30, 2010, pp. 1-14.
"PCT International Search Report and Written Opinion," from International Application No. PCT/US2012/040186, mailed Sep. 5, 2012, pp. 1-13.
"Restriction Requirement," for U.S. Appl. No. 13/483,387, mailed Feb. 4, 2014 (7 pages).
"Restriction Requirement Response," for U.S. Appl. No. 13/483,387, filed Mar. 31, 2014 (8 pages).
"Restriction Requirement," for U.S. Appl. No. 13/483,394, mailed Feb. 26, 2014 (7 pages).
"Restriction Requirement Response" for U.S. Appl. No. 13/483,394, filed Apr. 25, 2014 (7 pages).
Non-Final Office Action, for U.S. Appl. No. 14/811,901, mailed May 20, 2016 (16 pages).
Response to Non-Final Office Action, for U.S. Appl. No. 14/811,901, filed Jul. 27, 2016 (11 pages).

* cited by examiner

IMPLANTED LEAD ANALYSIS SYSTEM AND METHOD

This application claims the benefit of U.S. Provisional Application No. 61/734,198 filed Dec. 6, 2012, the content of which is herein incorporated by reference in its entirety.

FIELD OF THE INVENTION

The technology disclosed herein generally relates to implanted leads. More particularly, the technology disclosed herein relates to systems and methods for analyzing implanted leads.

BACKGROUND

Implantable medical devices are commonly used to treat and monitor patients with various medical conditions. Implanted medical devices used in the treatment and monitoring of heart conditions, for example, generally has a hermetically sealed housing that holds at least a power source and processor, as well as one or more leads running from the housing to locations in or about the heart. One or more electrodes along each lead provide electrical sensing and/or stimulating functionality to the heart from the housing.

Over time there can be wear and tear on a lead based on its durability and its environment, which can cause functionality problems such as inaccurate sensing, inaccurate treatment, and the like. As such, it is desirable for caregivers to be able to accurately identify a problematic lead with the information available, while minimizing "false positive" identification of problematic leads.

SUMMARY OF THE INVENTION

The technology disclosed herein relates to an external device for determining a lead-related condition associated with an implantable medical device (IMD). The external device generally has a communication module, a processing module, and a notification module. The communication module is configured to retrieve patient data from an IMD, where "patient data" includes at least episode data records and a summary data record. Each episode data record is generally associated with an episode and the summary data record corresponds to one or more episodes. The processing module executes rapid sensing analysis. Rapid sensing analysis generally includes the periodic retrieval of a summary data record from an IMD. The retrieval can be executed by a communication module. Rapid sensing applies episode selection criteria to the summary data record to identify one or more episodes of interest, and retrieval is initiated from the IMD of one or more episode data records associated with each episode of interest. Noise detection criteria are applied to the one or more episode data records. The notification module is configured to generate an alert if the noise detection criteria are satisfied.

In other embodiment, a method for lead analysis for an implanted medical device is described. A summary data record is retrieved associated with one or more episodes from an implanted medical device through a communication module. Episode selection criteria are applied to the summary data record by a processing module. One or more episode data records are retrieved from the implanted medical device for one or more episodes for which the episode selection criteria was satisfied. Noise detection criteria is applied to the episode data record. Another step is generating an alert if the noise detection criteria are satisfied.

The technology disclosed herein also relates to an external device for determining a lead-related condition associated with an implantable medical device (IMD). The external device generally has a communication module, a processing module, and a notification module. The communication module is configured to retrieve patient data from an IMD, where "patient data" includes at least episode data records and a summary data record. Each episode data record is generally associated with an episode and the summary data record corresponds to one or more episodes. Each summary data record includes a shock indicator indicating whether a shock was delivered by the IMD for a particular episode and the episode selection criteria excludes episodes during which a shock was delivered by the IMD. The processing module executes rapid sensing analysis. Rapid sensing analysis generally includes the periodic retrieval of a summary data record from an IMD. The retrieval can be executed by a communication module. Rapid sensing applies episode selection criteria to the summary data record to identify one or more episodes of interest, and retrieval is initiated from the IMD of one or more episode data records associated with each episode of interest. Noise detection criteria are applied to the one or more episode data records. The notification module is configured to generate an alert if the noise detection criteria are satisfied.

The invention may be more completely understood and appreciated in consideration of the following detailed description of various embodiments of the invention in connection with the accompanying drawings.

DETAILED DESCRIPTION

Figure 1:
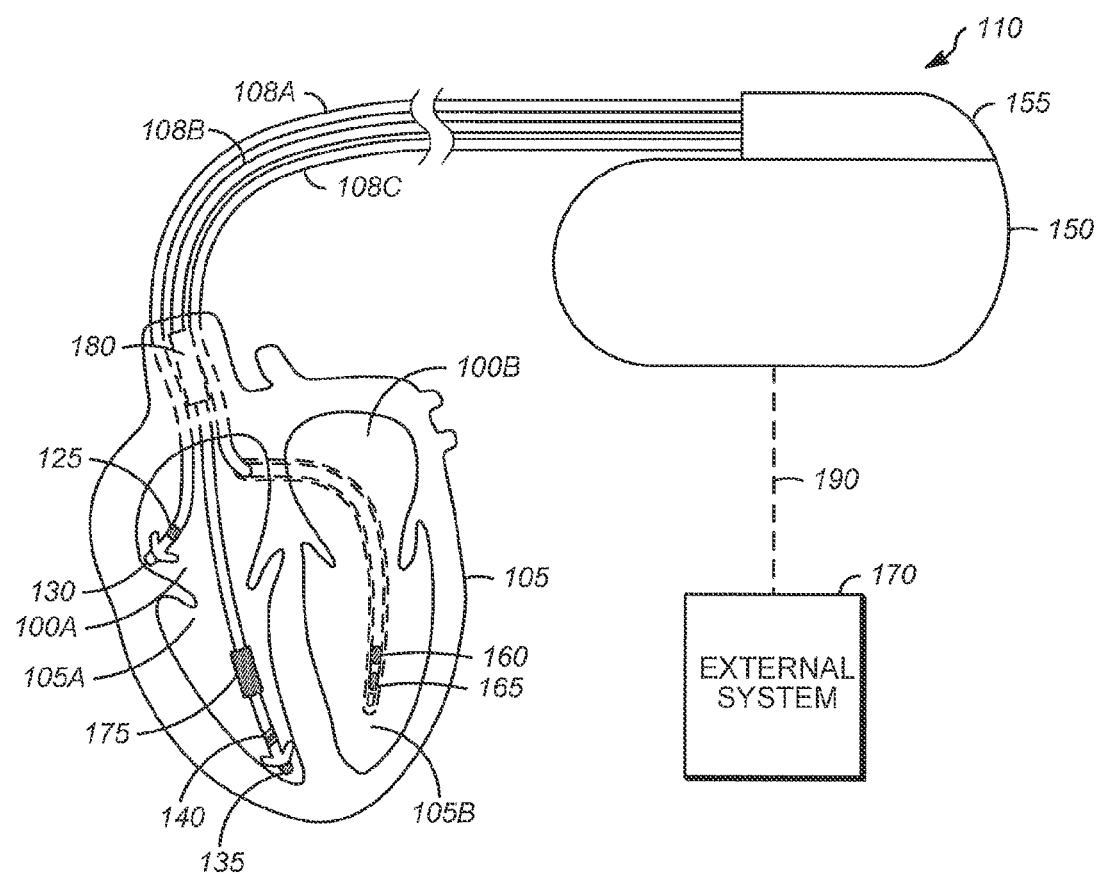
FIG. 1 depicts an example implementation of an implanted medical device, consistent with the technology disclosed herein.

FIG. 1 depicts an example implementation of an implanted medical device (IMD) 110, which is a cardiac rhythm management device. Examples of IMDs 110 include, without limitation, a pacer, a defibrillator, a cardiac resynchronization therapy (CRT) device, or a combination of such devices. The system also typically includes an IMD programmer or other external device 170 that communicates wireless signals 190 with the IMD 110, such as by using radio frequency (RF) or other telemetry signals. In one embodiment, the external device 170 communicates with the IMD at scheduled intervals to download information from the IMD. In one example, the external device 170 communicates once every 24 hours with the IMD. During a communication session, the IMD downloads information about the patient and any therapy delivered during the time interval since the previous communication session. The downloaded information can include a summary of any episodes that occurred during the time interval or a subset of those episodes. This summary information will be referred to herein as a summary data record or episode summary data. The summary data record and can include episode data records for specific episodes, such as episodes where a shock was delivered. The summary data record can include notification and alerts from the IMD along with many other types of information. Examples of information in the summary data record will be further described herein. Episode is defined to mean activity of a patient's body within a time period of particular interest, which is determined according to algorithms stored in the IMD. The time period can be a time when there is abnormal activity, for example, abnormal cardiac activity. One example of an episode of particular interest during lead analysis is a tachy episode, where the IMD algorithms indicate that the patient's heart is beating abnormally fast. The IMD 110 is coupled by one or more leads 108A-C to the heart 105. Cardiac leads 108A-C include a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

The heart 105 includes a right atrium 100A, a left atrium 100B, a right ventricle 105A, a left ventricle 105B, and a coronary sinus extending from right atrium 100A. The atrial lead 108A includes electrodes (electrical contacts, such as ring electrode 125 and tip electrode 130) disposed in the right atrium 100A of heart 105 for sensing signals, or delivering pacing therapy, or both, to the right atrium 100A.

The ventricular lead 108B includes one or more electrodes, such as tip electrode 135 and ring electrode 140, for sensing signals, delivering pacing therapy, or both sensing signals and delivering pacing therapy. The lead 108B optionally also includes additional electrodes, such as for delivering atrial cardioversion, atrial defibrillation, ventricular cardioversion, ventricular defibrillation, or combinations thereof to the heart 105. Such electrodes typically have larger surface areas than pacing electrodes in order to handle the larger energies involved in defibrillation. The lead 108B optionally provides resynchronization therapy to the heart 105.

The IMD 110 may include a third cardiac lead 108C attached to the IMD 110 through the header 155. The third cardiac lead 108C includes ring electrodes 160, 165 placed in a coronary vein lying epicardially on the left ventricle (LV) 105B via the coronary vein 120.

The lead 108B may include a first defibrillation coil electrode 175 located proximal to tip and ring electrodes 135, 140 for placement in a right ventricle (RV), and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD can 150. This improves defibrillation by delivering current from the RV coil 175 more uniformly over the ventricular myocardium. In some examples, the therapy is delivered from the RV coil 175 only to the electrode formed on the IMD can 150.

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrical contacts or "electrodes." Sensing among different sets of electrodes often provides directional information regarding the propagation of cardiac signals and is often referred to as sensing among different vectors. For example, in a single chamber ICD, sensing from a right ventricular tip electrode 135 to a right ventricular ring electrode 140 would be a first vector, and sensing from an RV coil 175 to an electrode on the can 150, or a header 155, would be second vector. Various electrode configurations may be used.

The electrode configuration used in the systems and methods described herein allow for the collection of patient episode data including electrograms (EGMs) on at least the right ventricular channel, while multiple channels may be used. The right ventricular EGM signal is recorded with electrodes implanted in or near a ventricle. For example, a ventricular channel or vector may include a tip electrode and ring electrode for the right ventricular channel or ring electrodes for the left ventricular channel. Another channel, known as the shock channel or shock vector, may be used. The shock channel is sensed using electrodes that are also used to delivery high-energy shock therapy. In one example, the shock channel includes an electrode placed in the RV.

As will be described with reference to FIG. 13, the IMD has a processor and memory to store patient episode data to be uploaded by a communication module. The IMD can overwrite the memory as necessary to store new patient episode data.

As will be appreciated by those having skill in the art, over the life of the patient the leads 108A-108C can experience general wear and tear, based on its own durability and its environment. Such wear and tear can cause functionality problems such as inaccurate sensing, inaccurate treatment, and the like. As such, it is desirable for caregivers to be able to accurately identify a problematic lead with the information available, while minimizing "false positive" identification of problematic leads.

Figure 2:
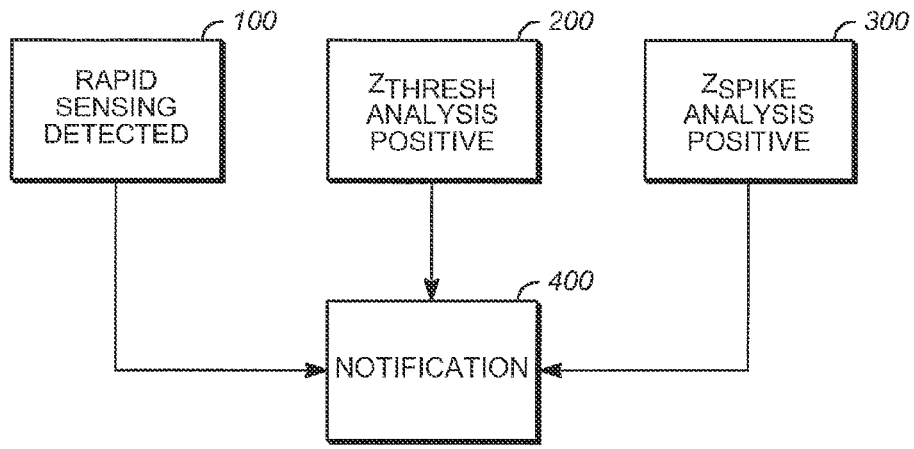
FIG. 2 depicts a schematic consistent with the notification technology disclosed herein.

FIG. 2 depicts a schematic consistent with the technology disclosed herein. Notification 400 of an issue arising from a suspect lead is provided to a patient, caregiver, or the like, if rapid sensing is detected 100, an impedance threshold analysis is positive 200, or an impedance spike analysis is positive 300. Notification 400 is generally that a lead condition has been identified through the rapid sensing 100, impedance threshold analysis 200, or impedance spike analysis 300. The analyses are generally conducted with a processing module. In a variety of embodiments, the lead is an implanted lead consistent with an implanted cardiac rhythm management device depicted in FIG. 1. The discussion of FIGS. 3-6 below particularly discuss methods consistent with rapid sensing, while the discussions of FIGS. 7 and 8 particularly discuss methods consistent with impedance threshold analysis and impedance spike analysis, respectively.

In one embodiment, impedance threshold analysis 200 is performed by a processor in the IMD while impedance spike analysis 300 and rapid sensing detection 100 is performed by a processor in an external device. However in another embodiment, analyses 100, 200 and 300 are performed by the IMD. In another embodiment, analyses 100, 200 and 300 are performed by the external device.

Notification 400 can generally be consistent with that known in the art through a patient and/or caregiver system interface, e-mail, and the like. Notification 400 will generally be accomplished by one or more notification modules. Where the analysis is performed in the external device that prompts the notification 400, notification 400 will generally be in real time immediately subsequently to the analysis being performed and include a timestamp of the episode that triggered the notification 400. The system can also be configured to store the notification and timestamp and analyze data based on the timestamp, and other data associated with each notification 400, which can be referred to as a notification record. Notification 400 by the external device will be described in more detail, below.

Where an analysis leading to notification is performed by the IMD, the notification can be part of the episode summary information that is downloaded to the external device during a communication session.

Figure 3:
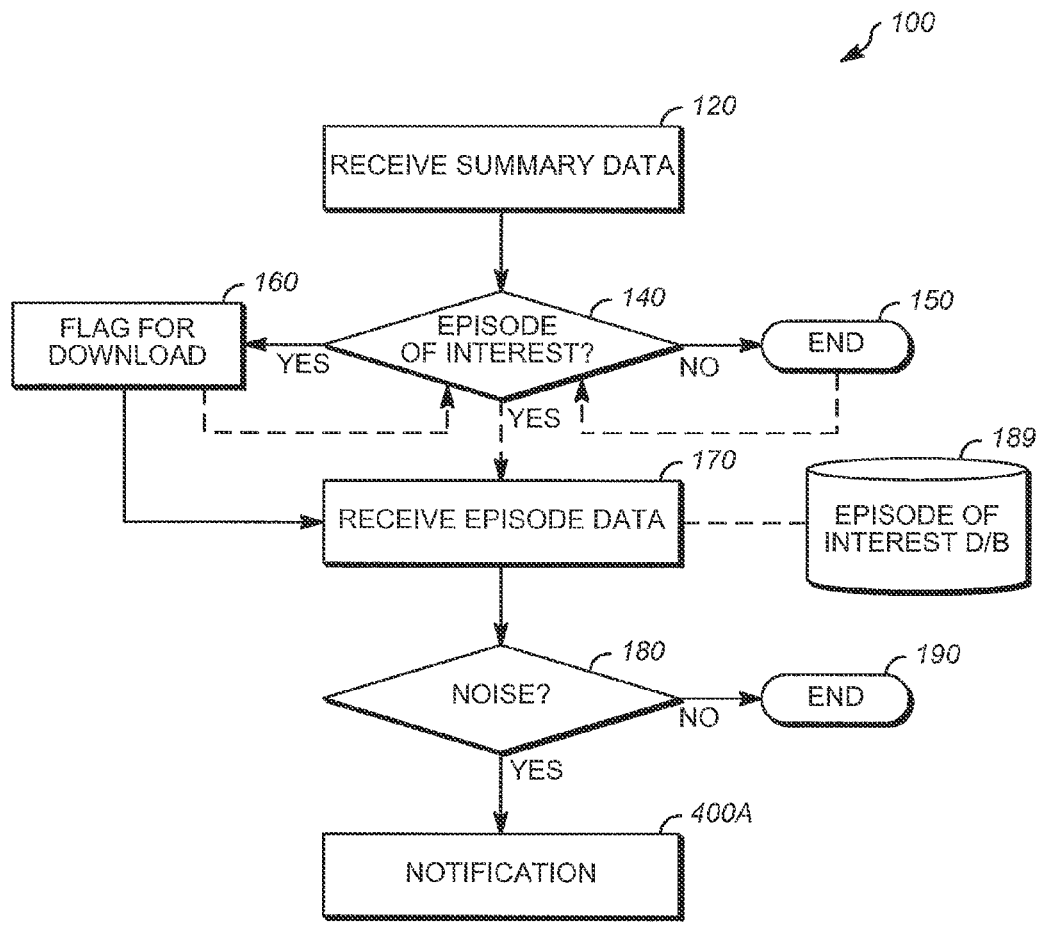
FIG. 3 depicts an example high level schematic associated with rapid sensing detection.

FIG. 3 depicts an example high level schematic associated with rapid sensing detection 100 of FIG. 2. In a communication session between the IMD and the external device, a summary data record is received 120 for one or more episodes, and an episode of interest determination is made 140 for each episode in the summary record. If the episode is not of interest, the analysis ends 150. If the episode is of interest, the episode is either flagged for upload 160 and then episode data is received 170, or the episode data is received 170 without first being flagged 160. Once the episode data record is received by the external device, a noise determination is made 180, and if there is noise, notification 400A follows. If there is no noise, the analysis ends 190.

In a variety of embodiments, episode summary data includes data that is typically received by a communication module from an IMD, as is known in the art. Episode summary data can include, for example, the following data for a particular episode: episode duration, episode zone, indication that the episode is non-sustained, indication that the episode is sustained, number of therapy attempts, type of therapy attempt (also referred to as a therapy indicator), whether episode therapy was commanded, time of day of the episode, episode number, and type of episode, as examples. The summary data for a particular episode is then analyzed to identify whether the episode is an episode of interest 140.

Typically a communication module associated with an IMD will upload episode summary data from the IMD in batches of a plurality of episode summaries based on the episode summary that was last uploaded. Each batch of episode summary data is included in a summary data record. The episode summary data that was last uploaded can be identified by, for example, an episode number. In a variety of embodiments, each episode summary in the batch of the plurality of episode summaries is analyzed individually to make a determination whether the episode is an episode of interest 140. If the episode summary does not identify the episode as an episode of interest 140, the analysis of that episode summary ends, and the next episode summary in the batch is considered. If the episode summary does identify the episode as an episode of interest 140, the episode is flagged for upload in the future, and the next episode summary data is analyzed to see if it is an episode of interest 140. Such analysis is continued until all of the summary data associated with the batch of episodes have been considered.

Figure 5:
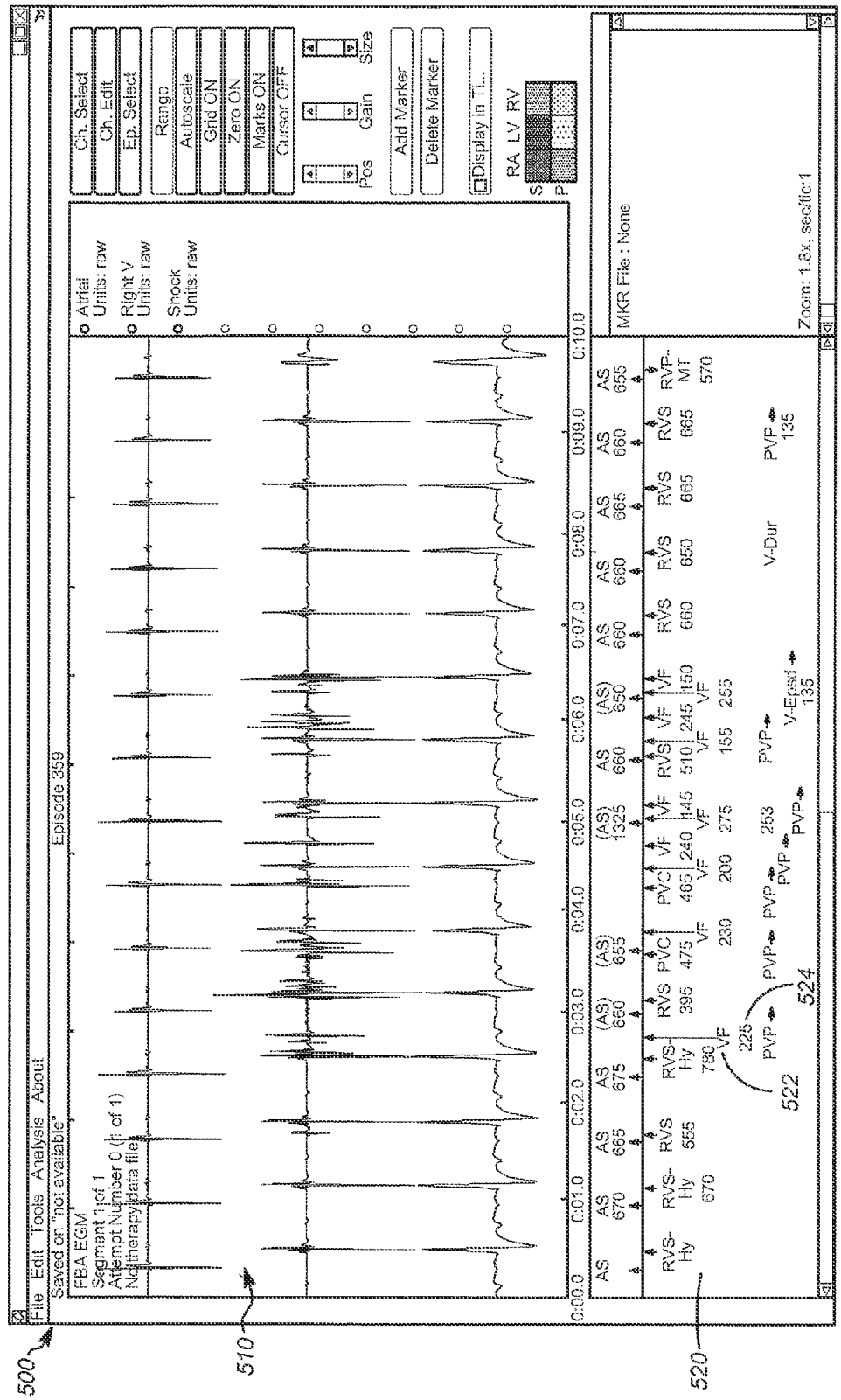
FIG. 5 depicts a portion of an example episode data record.

Once the summary data associated with each episode in the batch of episode summaries have been considered, the episode data associated with each of the flagged episodes is received 170 in a batch upload from the IMD. The episode data is then analyzed for noise 180, which is described in more detail in the discussion associated with FIG. 6. In some embodiments the episode data for each episode is an electrogram. In a variety of embodiments the episode data includes marker and summary data associated with an electrogram. In a variety of embodiments the episode data is an electrogram as well as episode markers associated with the electrogram. An example electrogram having associated markers is depicted in FIG. 5, which is described in more detail, below.

In example alternate embodiments, episode data for each episode of interest is received 170 when the episode of interest 140 determination is made. In such embodiments the episode data is not received 170 in batches. In some embodiments the noise analysis 180 can likewise be done on a per-episode basis rather than a batch-basis.

If noise is not identified 180 in the episode data, then the analysis ends 190. If noise is identified 180 in the episode data, then there is notification 400A. The notification 400A can generally convey to the system user that noise was detected, and can include a timestamp of the episode that triggered the alert and a summary of the episode. In an example notification 400A the system alerts the user to check a lead because a possible right ventricular non-physiological signal was detected on a particular date at a particular time. In a variety of embodiments, the data associated with the notification 400A is saved by the system for future reference. In a variety of embodiments, once notification 400A of noise associated with a particular episode on a particular date has been made, no further noise analysis is initiated on episodes occurring before that particular date. Such analysis may be considered redundant in some systems.

Figure 4:
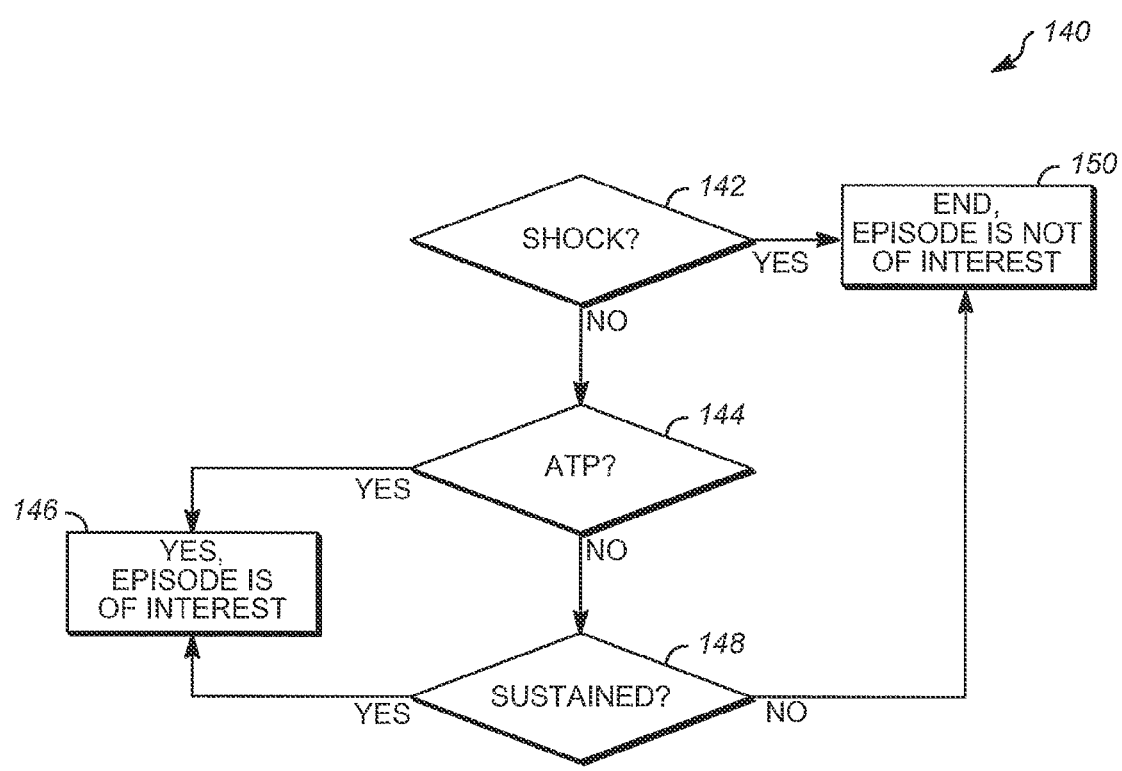
FIG. 4 depicts an example schematic associated with identifying an episode of interest.

FIG. 4 depicts an example schematic associated with identifying an episode of interest 140 of FIG. 3 based on episode selection criteria 142, 144, 148. The episode selection criteria 142, 144, 148 are applied to the retrieved episode summary data to determine whether a particular episode is an episode of interest. Such analysis can be executed by a processing module, for example. Specifically, the episode summary data for each episode is examined to identify whether a shock was delivered during that episode 142, and if a shock is identified, the analysis ends 150. If a shock is not identified, the summary data is examined to identify anti-tachycardia pacing (ATP). If ATP is identified, the episode data is identified as of interest 146. If ATP is not identified, the summary data is examined to identify whether the episode was sustained 148. If the episode was not sustained, the analysis 140 ends 150. If the episode was sustained, then the episode is identified as of interest 146.

If episode summary data indicating that a shock was administered is identified 142 the analysis of the summary data ends 150, and the episode is not identified as an episode of interest. In a variety of systems, episodes resulting in the administration of a shock 142 to a patient are currently afforded a relatively high level of scrutiny based on the high impact of the shock on the patient and the potentially dangerous physiological state experienced by the patient. Further, administration of an improper shock treatment to the patient is typically examined with haste after the occurrence. As such, notification of noise associated with episodes leading up to a shocked treatment might often be a redundant inquiry. In one alternate embodiment, however, episodes where a shock was administered can be considered an episode of interest.

If episode summary data indicating that ATP was administered is identified 144 the episode is determined to be an episode of interest 146, and can be flagged for upload. If ATP is not identified 144 in the episode summary data, then the episode summary data is analyzed to identify whether the episode was sustained 148. If the episode summary data does not identify the episode as sustained, then analysis of the summary data ends 150, and the episode is not identified as an episode of interest. If the episode summary data does identify the episode as sustained, then the episode is identified as an episode of interest 146 and the episode is either flagged for upload or retrieval of the episode data is initiated from the IMD.

In a variety of embodiments of the current process, non-sustained episodes are not considered in the noise analysis 100 to conserve system resources such as IMD battery life and processing bandwidth. This is because non-sustained episodes generally occur at a relatively high frequency when compared with sustained episodes. For purposes of this application, a "sustained episode" is defined as an episode that meets minimum time requirements. For example, a "sustained episode" may be defined in one embodiment as where eight out of ten beats are faster than a programmed rate threshold and then six out of ten beats remain faster than the programmed rate threshold, which is maintained for a programmed length of time.

Generally the programmed length of time can range from about 1 second to about 60 seconds and the programmed rate threshold can range from about 160 beats per minute (bpm) to about 200 bpm. In a variety of embodiments the programmed length of time ranges from about one second to about 2.5 seconds. In some embodiments the programmed length of time is one second. In some embodiments the programmed length of time is two seconds. In some embodiments the programmed length of time is up to sixty seconds. In some embodiments the programmed rate threshold is 160 bpm. In some embodiments the programmed rate threshold is 180 bpm. In some embodiments the programmed rate threshold is 200 bpm.

As described above with reference to FIG. 3, there can be a batch of episode summaries that are uploaded for consideration and each episode summary in the batch is analyzed according to the process steps reflected in FIG. 4 to determine whether the episode is an episode of interest. In a variety of embodiments, the system is configured to assess episode summaries that have not yet been considered. As such, the system can be configured to store identifying data for the last episode considered, such as episode number, and assess episode summaries for episodes occurring subsequent to that last episode.

Referring back to FIG. 3, retrieval of episode data 170 from the IMD is initiated for the episodes of interest. In a variety of embodiments retrieval of episode data 170 is initiated by the communication module of the external device. In a variety of embodiments, the episode data is an electrogram. In a variety of embodiments the episode data is stored in an episode of interest database 189 for access and analysis. The episode of interest database 189 may be part of memory of the external device in one embodiment. The episode of interest database may also be part of a different external memory location, such as a memory location of a patient management system.

FIG. 5 depicts a portion of example episode data 500, which is also referred to herein as an episode data record 500. This particular episode data 500 has an electrogram portion 510 and an associated marker portion 520. Generally, an IMD consistent with the currently-described technology determines locations of heart beats within the EGM data 510, resulting in a group of device-identified beat locations that are device markers 520. The EGM portion 510 is generally a graphical representation of the patient's cardiac activity and the marker portion 520 marks detected events corresponding to the EGM portion 510. Among other data, the marker portion 520 can indicate beat-specific data such as the heartbeat zone 522, heartbeat time 524, pacing therapy (not shown), a diverted shock (not shown), and event detection, as examples. Those having skill in the art will appreciate the other types of marker data 520 that can be provided.

The EGM data 510 and markers 520 are stored in a memory of the IMD. Once the episodes of interest are determined by a process consistent with FIGS. 3 and 4, the communication module initiates retrieval of the episode data record for episode of interest 500 from the IMD. The episode data 500 is then analyzed in the noise analysis 180 of FIG. 3, which is described in more detail now with reference to FIG. 6. In one embodiment, the noise analysis 180 utilizes the marker portion 520 of the episode data record and does not utilize the EGM portion 510 of the episode data record.

By using summary data and episode data currently provided by IMDs to external devices, it is possible in one embodiment to perform the noise analysis described here in without any alterations being required to IMDs or the programming of the IMDs that are coupled to systems consistent with the technology disclosed herein. Furthermore, changes to the analysis disclosed herein can be made readily in the processing module that is external to the IMD, as the situation necessitates.

Figure 6:
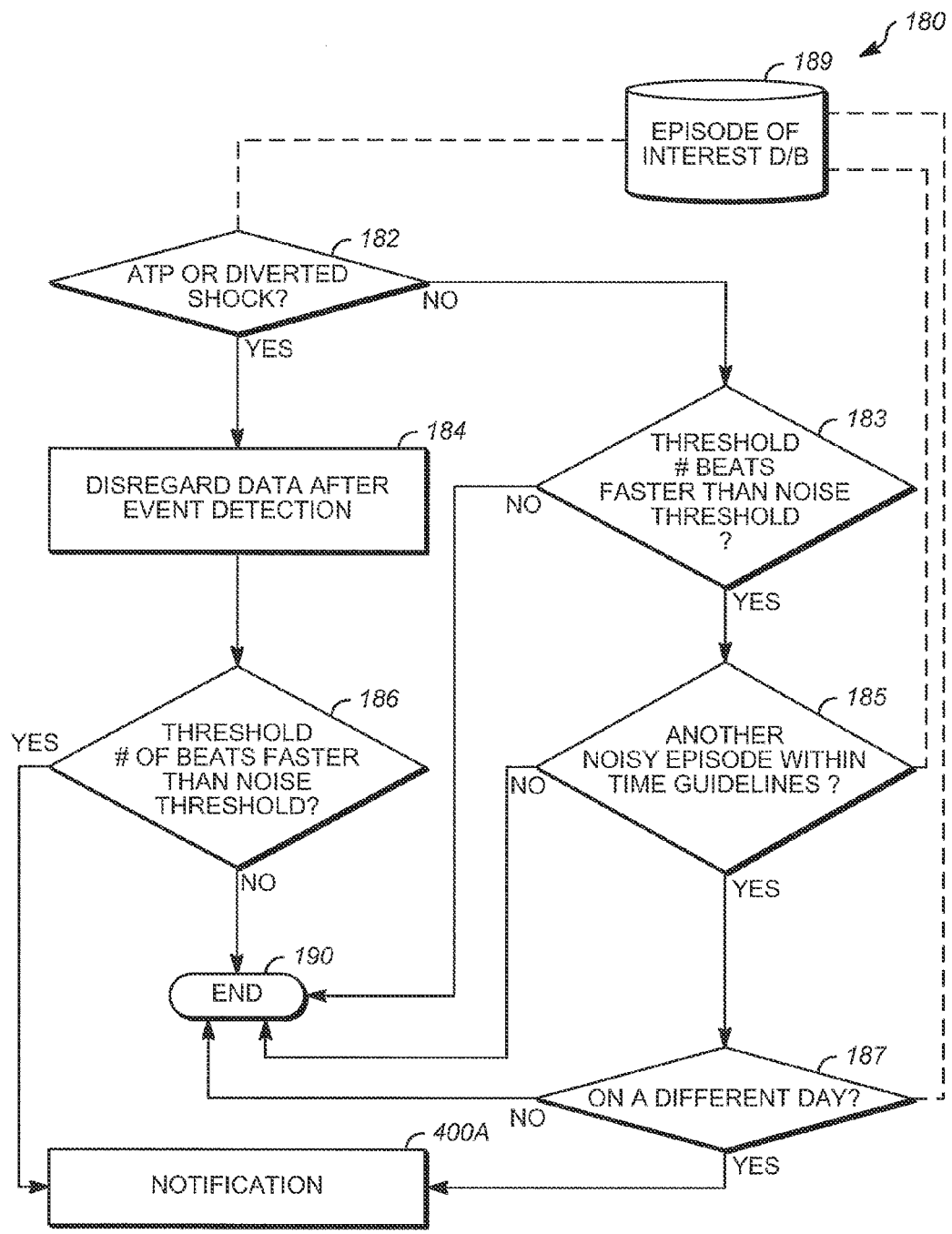
FIG. 6 depicts an example schematic associated with noise analysis for episodes of interest.

FIG. 6 depicts an example schematic associated with noise analysis 180 from FIG. 3. Such analysis can be executed by a processing module, for example. The episode data can be from the episode of interest database 189. A number of different analysis steps will be described that are performed using the episode data. Although these steps have been presented in a particular order for one embodiment, it is also possible to change the order of these analysis steps.

In one step of the analysis, an episode data record associated with a particular episode is examined for ATP or diverted shock 182. If ATP or diverted shock 182 is identified, data is disregarded after event detection marker 184 for a threshold analysis 186. In the threshold analysis 186 it is determined whether a threshold number of beats are faster than the noise threshold 186. If the answer to the threshold analysis 186 is yes, there is notification 400A. If the answer to the threshold analysis is no, then the analysis ends 190.

If, on the other hand, ATP or diverted shock 182 is not identified, the episode data is to determine if the episode data meets the noise definition of the system. The episode data is analyzed to find a threshold number of sensed ventricular beats faster than a first fast interval threshold or noise threshold 183. If such a threshold is not met, the analysis ends. If the threshold is met, the process looks for another noisy episode 185 on a different day 187 that also satisfies the noise definition. If there has not been another noisy episode 185, or the episode was on the same day 187, the analysis ends 190. If there has been another noisy episode 185 on a different day 187, notification 400A follows. The process uses one or more databases 189 that provide data associated with episodes of interest.

Identification of ATP 182 can include considering the EGM markers from the episode data for a marker that indicates ATP. Similarly, identification of a diverted shock 182 can include considering the EGM markers from the episode data for a marker that indicates a diverted shock. In some embodiments, episodes with ATP or a diverted shock are identified by a marker in the episode data that marks an event detection resulting in the ATP or diverted shock. An event detection marker or "detection met" marker indicates that the IMD has decided that a cardiac event has occurred, according to the IMD's programmed criteria, which warrants that some type of therapy be provided to the patient. Examples of therapy that can be provided to the patient include shock or ATP, among others. In some situations, the criteria for a shock is satisfied, resulting in an event detection marker and the IMD initiating charging to deliver a shock, but the IMD decides not to deliver the shock and so diverts the shock. In some embodiments, these episodes will have a marker indicating that the shock was diverted. If there are no markers in the episode data that indicate either ATP or diverted shock, then the episode is an untreated sustained episode, since the previously-executed analysis, depicted in FIG. 4, rules out episodes that are non-sustained or that included a therapeutic shock.

If the episode data includes a marker for either ATP or diverted shock 182, a noise analysis is conducted 186 that disregards the episode data after the event detection 184. In a variety of instances, episode data collected during or after administered therapy can cause particularly fast heart beats that may be interpreted by the system as "noise." As such, it may improve the predictive value of the system to ignore such data. Additionally, focusing on physiological data that triggers an event detection to warrant a diverted shock can allow a system user to improve system analytics.

The threshold analysis 186 determines whether the episode meets the noise detection criteria. Particularly, the threshold analysis determines whether, before the event detection, there are a threshold number of beats that are each faster than a beat length threshold 186. In at least one embodiment, the threshold number of beats is four and the beat length threshold is about 160 milliseconds. Stated differently, the noise detection criteria are satisfied if, before event detection, the system identifies at least four beats that are 160 ms or less in length. Those having skill in the art will recognize other numbers of beats occurring at alternate beat length thresholds may also be accurate predictors of an issue with a lead. In a variety of embodiments, the system is configured to store the outcomes associated with the application of noise detection criteria to retrieved episode data records.

The analysis for untreated sustained episodes is similar to the analysis of episodes with ATP or diverted shock in that the episode data is considered to identify a threshold number of beats that are faster than a threshold beat length. If this threshold criteria 183 is met to indicate that the episode was noisy, notification criteria for untreated sustained episodes further requires that a second noisy episode be identified 185. The second noisy episode 185 need be identified as occurring within the time period since the last notification 400A or within the last thirty days, whichever is less. In other words, an episode counter that is configured to count the number of untreated sustained episodes is restarted at notification 400A, where the notification 400A is only notification 400A associated with rapid sensing 100. Additionally, the second noisy episode need be on a different day 187 than the first noisy episode. Such notification criteria 185, 187 improve the predictive value of the notification 400A for lead problems by limiting the likelihood that the sensed noise is caused by the environment the patient is in.

As mentioned above, the process uses one or more episode databases 189 that provide data associated with episodes of interest. In a variety of embodiments, when an episode is identified as meeting the noise criteria 183, such identification is saved in the episode database 189. In a variety of embodiments, when an episode is identified as meeting the noise criteria 183, such identification is counted on a noisy episode counter which counts noisy episodes within the last 30 days and resets upon notification 400A.

Figure 7:
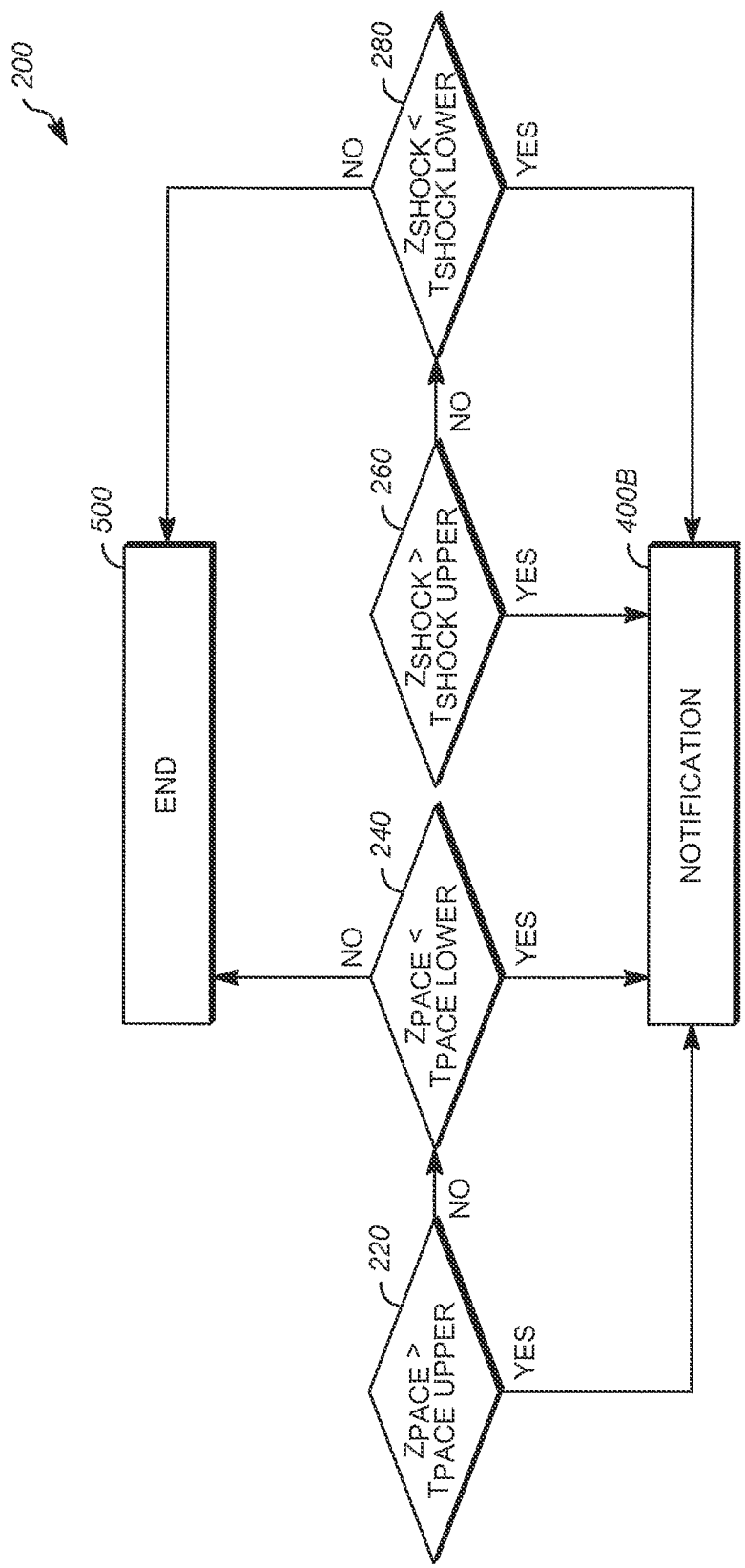
FIG. 7 depicts an example schematic associated with impedance threshold analysis.

FIG. 7 depicts an example schematic associated with impedance threshold analysis. Such analysis can be executed by a processing module, for example. In at least one embodiment, such analysis is executed by an IMD. Pacing/sensing lead impedance $Z_{pace}$ is analyzed to determine whether it is greater than an upper pacing impedance threshold $T_{pace-upper}$ 220 or less than a pacing/sensing lead lower impedance threshold $T_{pace-lower}$ 240. If the answer to either analysis 220, 240 is "yes," then notification 400B follows. If the answer to both analysis is "no," then the analysis ends 500. Similarly, shock lead impedance $Z_{shock}$ is analyzed to determine whether it is greater than an upper shock impedance threshold $T_{shock-upper}$ 260 or less than a lower shock impedance threshold $T_{shock-lower}$ 280. If the answer to either analysis 260, 280 is "yes," then notification 400B follows. If the answer to both analysis 260, 280 is "no," then the analysis ends 500.

Generally the $T_{pace-upper}$ is about 2000Ω and the $T_{pace-lower}$ is about 200Ω. Generally $T_{shock-upper}$ is about 20Ω, and $T_{shock-lower}$ is about 125Ω. Those having skill in the art will appreciate that other values may be used that may improve predictive value of the notification 400B.

The notification 400B associated with a lead impedance measurement can generally convey to the system user of the lead at issue and whether the impedance measurement was above the threshold value or below the threshold value. If the resistance measurement is above the threshold value, the notification 400B can include notifying the system user of possible lead breakage. If the resistance measurement is below the threshold value, the notification 400B can include notifying the system user of possible insulation failure. The notification 300 can also include a timestamp if the impedance measurement that triggered the alert and a summary of the event. In a variety of embodiments, the data associated with the notification 400B is saved by the system for future reference. In a variety of embodiments, once notification 400B that an impedance measurement taken on a particular day for a particular lead is outside the threshold, no further impedance threshold analysis is initiated for that lead on days occurring before that particular day. Such analysis may be considered redundant in some systems. In embodiments where impedance analysis is executed by an IMD, notification 400B can include communication with a communication module to provide the notification 400B to an external device. The notification 400B can be included with a summary data record that is retrieved from the IMD by an external device.

Many different impedance threshold analysis methods are known in the art and in alternate embodiments can be used in combination with the noise detection analysis and impedance spike analysis described herein.

Figure 8:
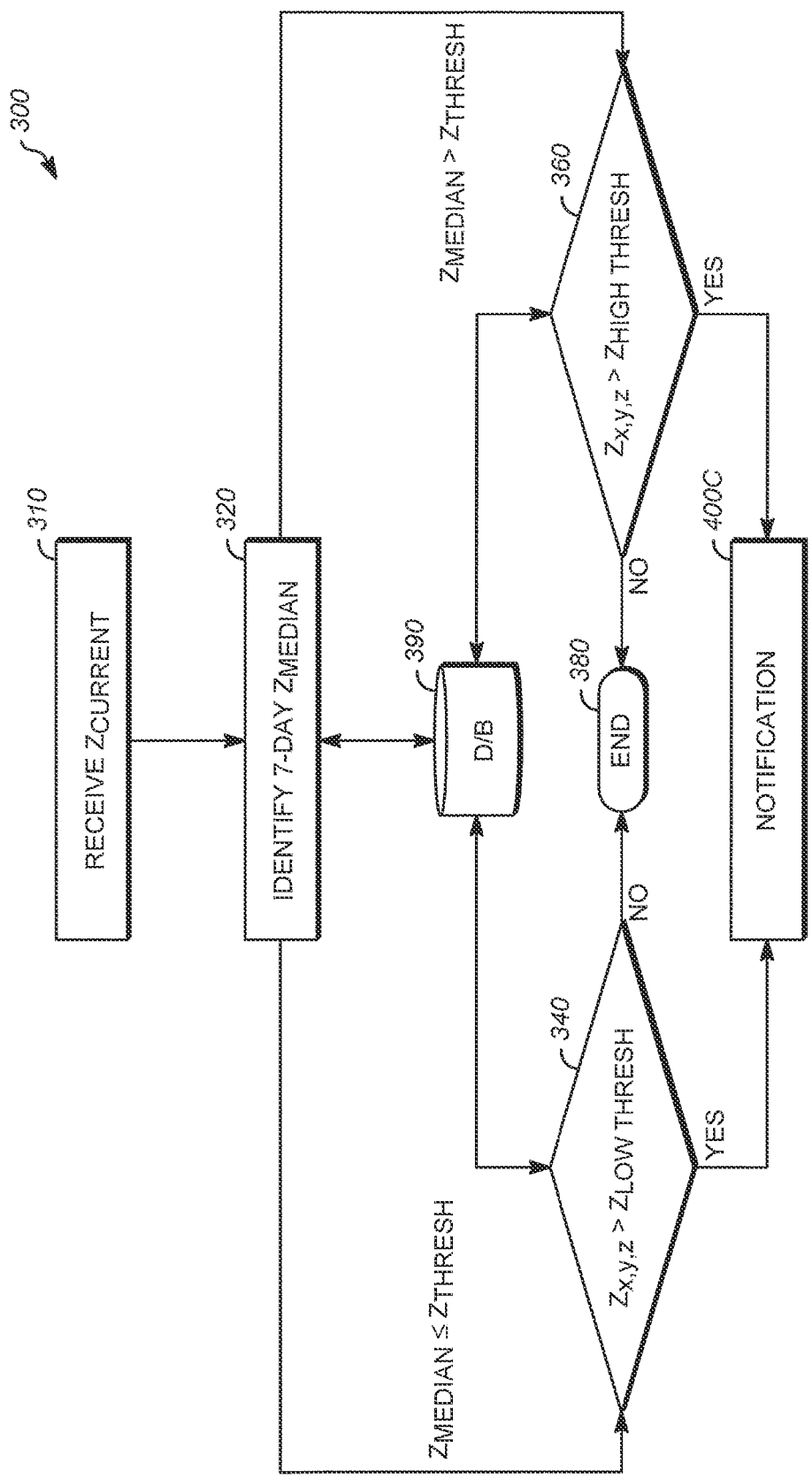
FIG. 8 depicts an example schematic associated with an impedance spike analysis.

FIG. 8 depicts an example schematic associated with an impedance spike analysis. Such analysis can generally be executed by a processing module. In one embodiment, the analysis is executed by a processing module of the external device. The current lead impedance $Z_{current}$ is received 310 and a 7-day impedance median $Z_{median}$ is determined 320. The system identifies a target number of impedance "spikes" relative to the impedance median $Z_{median}$. Particularly, the threshold impedance required to qualify as an "impedance spike" can vary based on the impedance median $Z_{median}$.

If the 7-day impedance median $Z_{median}$ is less than or equal to a threshold impedance $Z_{thresh}$, the system looks for three impedance spikes $Z_{x, y, z}$ that are greater than a first impedance threshold $Z_{low-thresh}$ 340. If the 7-day impedance median $Z_{median}$ is greater than the threshold impedance $Z_{thresh}$, the system looks for three impedance spikes $Z_{x, y, z}$ that are greater than a second impedance threshold $Z_{high-thresh}$ 360. If either analysis 340, 360 identifies three impedance spikes $Z_{x, y, z}$, then notification 400C follows. Notification can generally be accomplished by a notification module. If either analysis 340, 360 does not identify three impedance spikes $Z_{x, y, z}$, the analysis ends 380. One or more impedance databases 390 containing daily impedance data can be used in such an impedance spike analysis 300.

Generally the impedance spike analysis takes into account natural impedance spikes that can occur by virtue of the structure of the IMD absent relevant lead problems. For example, slight shifts of set screws used in the IMD can cause a spike in the impedance measurement of a particular lead. As such, by identifying three spikes in a seven day time period, the notification 400C of a lead condition has a higher predictive value that a single spike in the seven day time period. Those having skill in the art will appreciate that other time periods can be used other than the seven-day median, such as a five-day median or a nine-day median, as examples. Similarly, the analysis could also identify more or less impedance spikes to trigger notification 400C. The number of impedance spikes required to trigger notification 400C is referred to as a "spike threshold."

In some embodiments, the threshold impedance $Z_{thresh}$ is about 750Ω. In some embodiments, the first impedance threshold $Z_{low-thresh}$ is about 300Ω. In some embodiments, the second impedance threshold $Z_{high-thresh}$ is about 750Ω. Those having skill in the art will recognize that other values can be used for the various impedance thresholds that may improve predictive value of the analysis.

In a variety of scenarios the impedance data will be uploaded by the communication module from the IMD in a batch, depending on the last uploaded impedance data. In a variety of implementations of the current technology, receiving $Z_{current}$ will include impedance measurements up to the last fourteen days, even if it has been more than fourteen days since the last upload of impedance data. The impedance spike analysis 300 will then apply to each of the seven-day medians within the fourteen-day period. The analysis of the seven-day median does not include any day on which there was notification 400C or any day before notification 400C for a particular lead. In other words, the impedance spike analysis for a particular lead restarts upon notification 400C, where the notification 400C is only notification 400C associated with impedance spike analysis 300.

If three impedance spikes are not identified 340, 360 then the analysis ends 380. If three impedance spikes are identified 340, 360, then there is notification 400C. The notification 400C can generally convey to the system user that impedance spikes were detected, and can include a timestamp of the most recent measurement that triggered the alert and a summary. In an example notification 400C the system alerts the user to check a lead due to an abrupt change in the lead impedance in the past seven days, on a particular date at a particular time. In a variety of embodiments, the data associated with the notification 400C is saved by the system for future reference. In a variety of embodiments, once notification 400C of impedance spikes associated with a particular lead on a particular date has been made, no further impedance spike analysis is initiated on measurements occurring before that particular date. Such analysis may be considered redundant in some systems.

Figure 9:
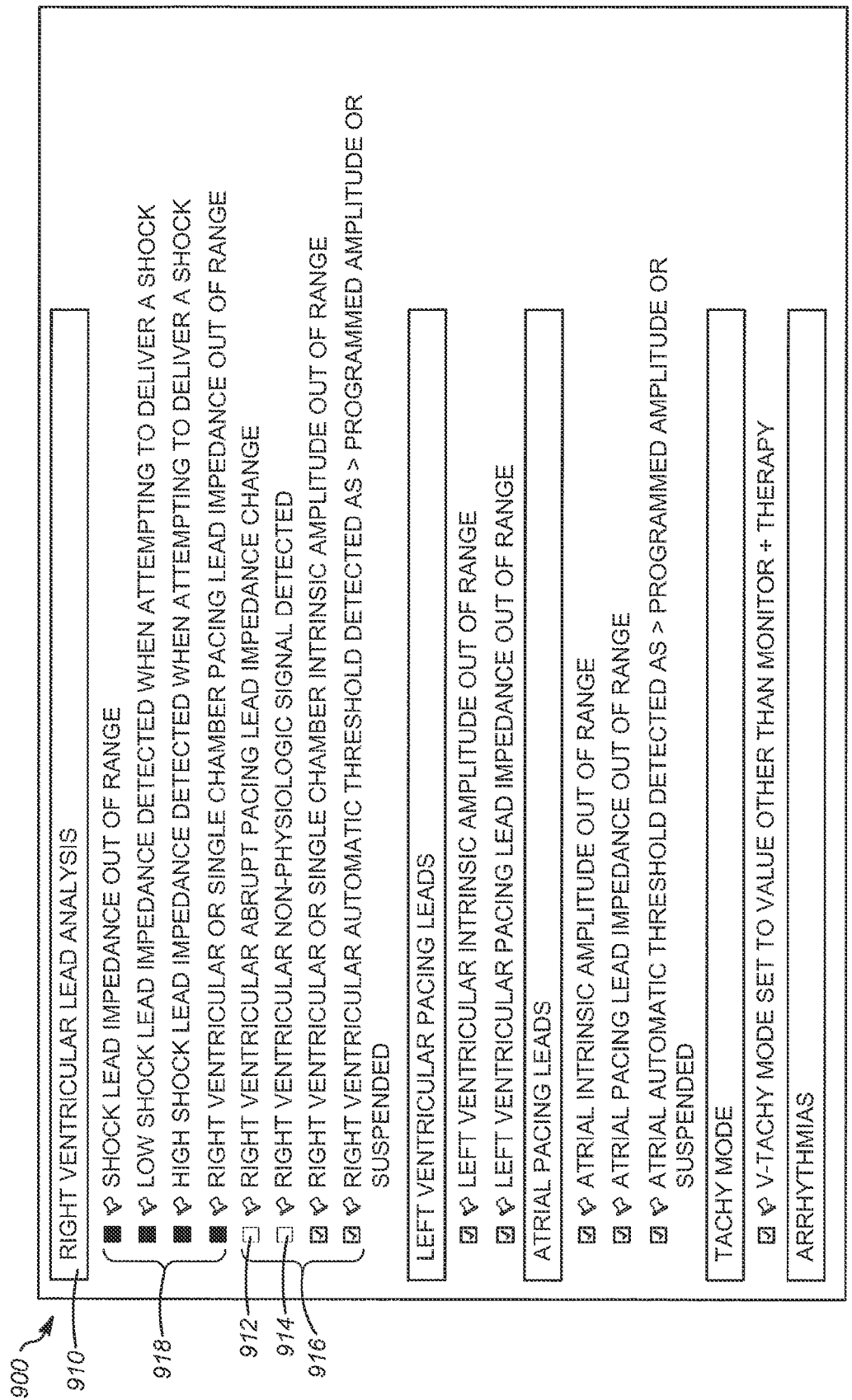
FIG. 9 depicts a screenshot of an example implementation of the technology disclosed herein.

FIG. 9 depicts a screenshot of an example implementation of the technology disclosed herein. In a variety of embodiments, such user interfaces 900 are consistent with the settings for an individual patient rather than clinic-wide settings so that operational changes for each patient can take into account particular hardware associated with the patient.

In a variety of embodiments, lead check settings 910 have some non-optional settings 918 and some others are optional settings 916. In some such embodiments, impedance spike analysis 912 and rapid sensing analysis 914 are two such optional settings 916. In at least one embodiment, the impedance spike analysis 912 and the rapid sensing analysis 914 default to "off". Such a default setting is desirable in situations where there is a high probability that any patient using such a system has IMD components that will not substantially benefit from lead analysis taught herein. For example, it may be determined that leads having a particularly low probability of failure will likely not benefit from such lead analyses, especially since the occurrence of a false positive could lead to unnecessary surgeries to replace leads.

In other embodiments, it may be desirable that the impedance spike analysis 912 and the rapid sensing analysis 914 default to "on," particularly where such a system is more likely to be used with patient's having IMD components that would benefit from such analysis, i.e. leads that have a reasonable risk of failure.

In a variety of embodiments the interface 900 does not provide the ability for the user to change the sensitivity of the impedance spike analysis 912 and the rapid sensing analysis 914.

Description of Hardware Systems

The above-described method can be implemented on various hardware systems, such as on a programmer, in a patient management system, or other computational devices.

Figure 10:
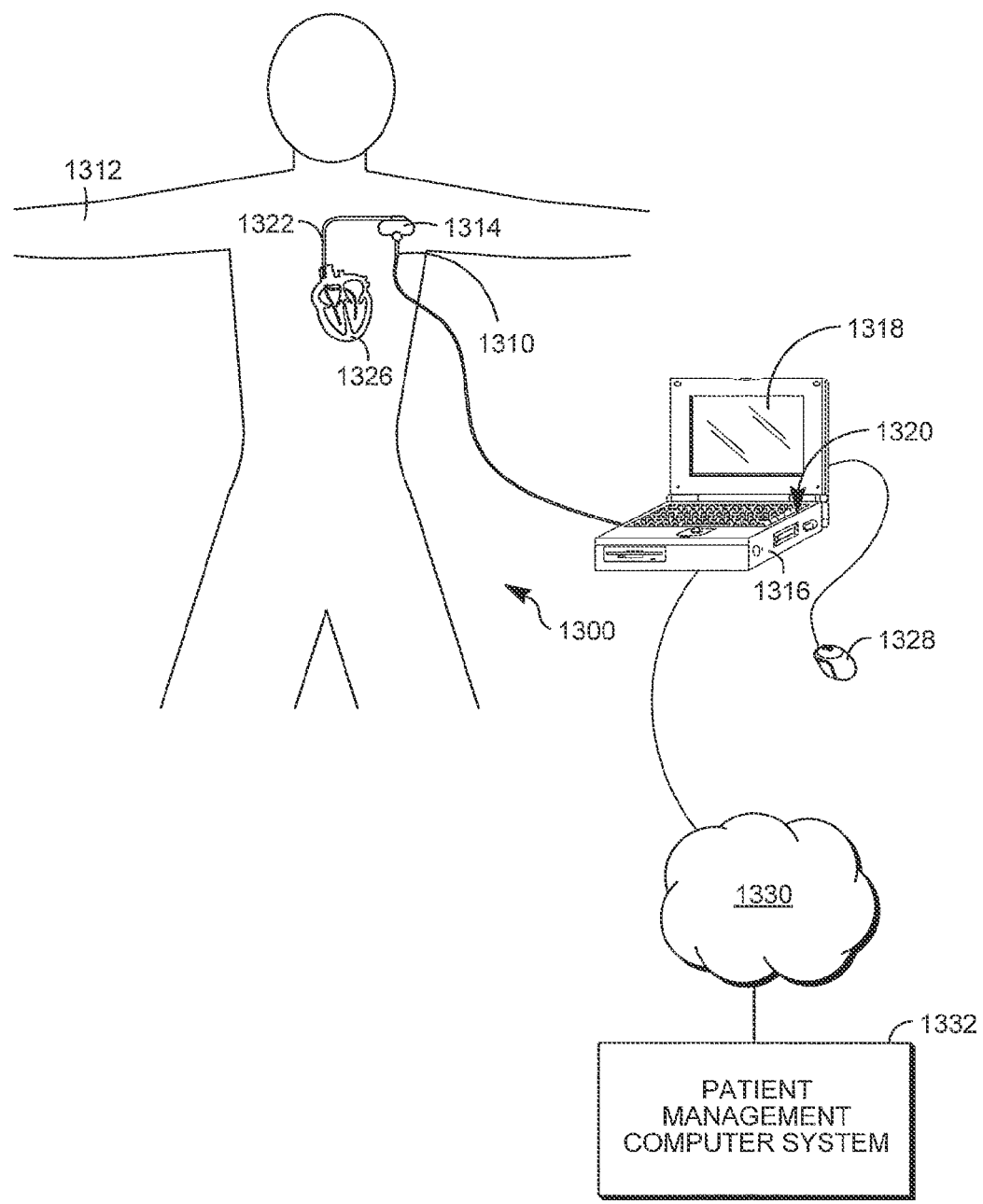
FIG. 10 depicts an example cardiac rhythm management system consistent with at least one implementation of the technology disclosed herein.

FIG. 10 is a schematic of an exemplary cardiac rhythm management (CRM) system 1300. The system 1300 can include an IMD 1314 disposed within a patient 1312. The IMD 1314 can include pacing functionality. The IMD 1314 can be of various types of devices such as, for example, a pacemaker, a cardioverter-defibrillator, a cardiac resynchronization device, a heart rhythm monitoring device, or the like. The IMD 1314 includes one or more leads 1322 disposed in or near the patient's heart 1326.

The IMD 1314 can be in communication with an external interface device 1316. In some embodiments, communication between the IMD 1314 and the external interface device 1316 can be via inductive communication through a wand 1310 held on the outside of the patient 1312 near the IMD 1314. However, in other embodiments, communication can be carried out via radio frequency transmission, acoustically, or the like. The particular device that is configured to retrieve data, including patient data, from the IMD 1314 is generally referred to as a "communication module."

The IMD 1314 can include one or more implanted sensors in order to gather data regarding the patient 1312. For example, the IMD 1314 can include an activity level sensor, a respiration sensor, a heart sounds sensor, a blood pressure sensor, an impedance sensor, or other sensors. The data gathered using the IMD 1314 may be any type of patient data. In a variety of embodiments, and as described above, the IMD 1314 collects electrograms from the patient. The patient data can further comprise data regarding the locations of heart beats within the electrograms. This data can be collected into groups of device-identified beat locations for each collected electrogram.

The IMD 1314 is generally configured to store data over a period of time, and periodically communicate with the external interface device 1316 in order to transmit some or all of the stored data.

The external interface device 1316 can be for example, a programmer, a programmer/recorder/monitor device, a computer, a patient management system, a personal digital assistant (PDA), or the like. As used herein, the term programmer refers to a device that programs implanted devices, records data from implanted devices, and allows monitoring of the implanted device. Exemplary programmer/recorder/monitor devices include the Model 3120 Programmer, available from Boston Scientific Corporation, Natick, Mass. The external interface device 1316 can include a user input device, such as a keyboard 1320 and/or a mouse 1328. The external interface device 1316 can include a video output channel and video output device, such as a video display 1318 for displaying video output. The displayed video output can include a user interface screen. In addition, the video display 1318 can also be equipped with a touch screen, making it into a user input device as well.

The external interface device 1316 can display real-time data and/or stored data graphically, such as in charts or graphs, and textually through the user interface screen. In addition, the external interface device 1316 can present textual information to a user along with several response options. The external interface device 1316 can also input and store a user's response to a question, and can store a user's text response in some embodiments.

In one embodiment, the external interface device 1316, which can also be referred to as a user interface, is in communication with a patient management computer system 1332. The communication link between the user interface 1316 and the patient management computer system 1332 may be via phone lines, the Internet 1330, or any other data connection. The user interface 1316 can also be used when it is not in communication with a device, but is only in communication with the patient management computer system 1332.

In one embodiment, the external interface device 1316 is capable of changing the operational parameters of the IMD 1314, and is therefore referred to as a programmer. Typically, programmers are used to interface with CRM devices in a clinic or hospital setting. In this context, the user of the external interface device 1316 is a physician or trained technician.

The components that execute the analysis as described herein are generally referred to as the "processing module." Those having skill in the art will appreciate that the processing module can include components of the patient management system 1332, the external interface device 1316, other devices, and combinations thereof. Similarly, the components of the system that generate notifications consistent with the technology disclosed herein are generally and collectively referred to as the "notification module," for purposes of this application.

Figure 11:
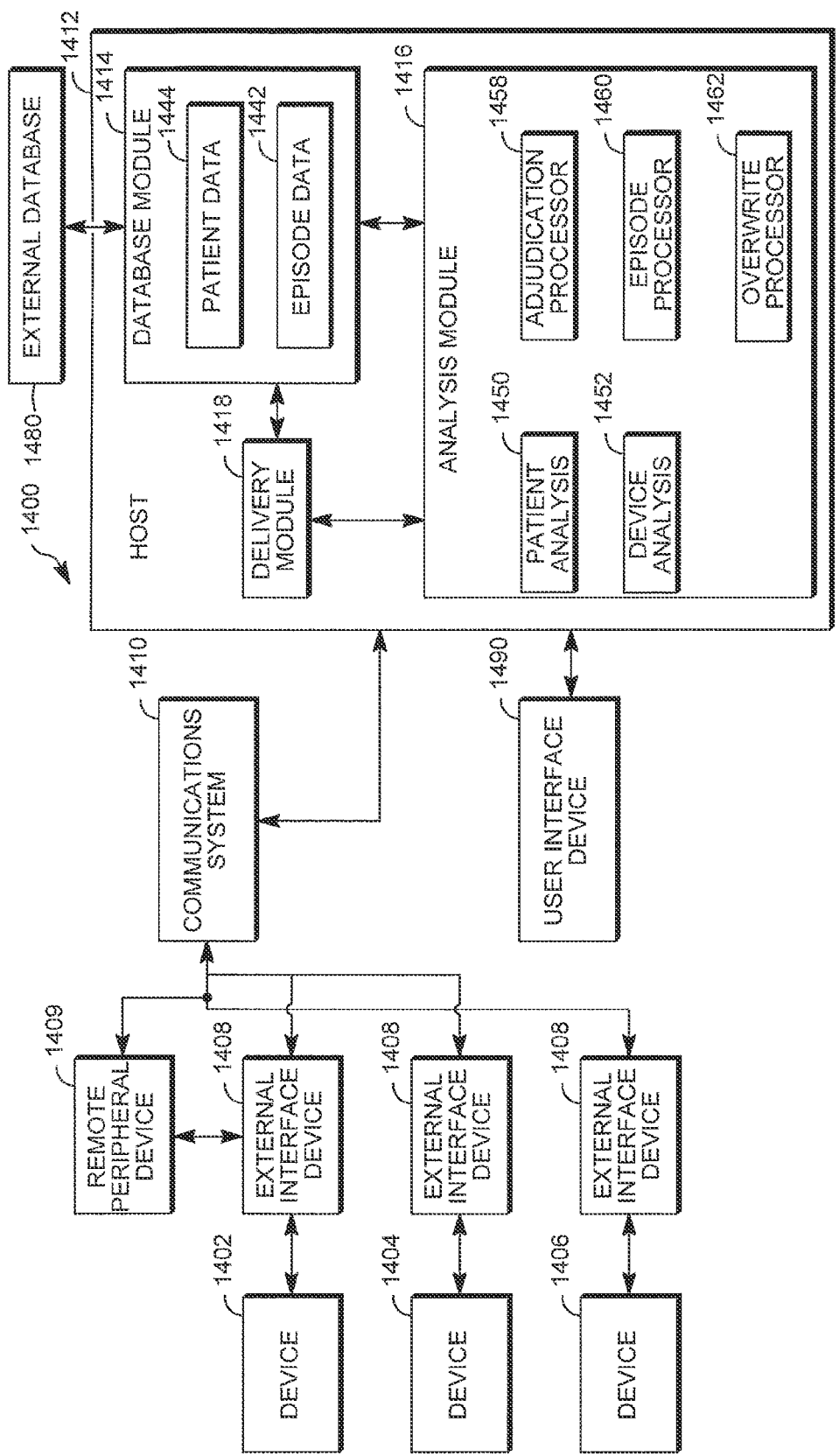
FIG. 11 depicts a schematic of a patient management system consistent with at least one implementation of the technology disclosed herein.

FIG. 11 is a schematic illustration of a patient management system consistent with at least one embodiment of the invention. The patient management system is capable of maintaining an episode database using computer storage medium. Of note, the episode database may also be present in an implantable or implanted device as discussed further herein. A computer storage medium is any technology, including devices and materials, used to place, keep and retrieve data. Examples of computer storage medium include random-access memory (RAM), a network-attached storage device, magnetic storage such as hard disk drives, optical discs, and a redundant array of independent discs (RAID).

Patient management system 1400 generally includes one or more devices 1402, 1404, and 1406, one or more external interface devices 1408, a communication system 1410, one or more remote peripheral devices 1409, and a host 1412. The host 1412 may be a single computing device, such as a programmer or other patient management device. In some embodiments, the host 1412 is an external device that communicates directly with the one or more devices 1402, 1404, and 1406 and does not require the use of separate external interface devices 1408. In some embodiments, the host is an external device and receives data, such as EGM data, from an external database 1480.

Each component of the patient management system 1400 can communicate using the communication system 1410. Some components may also communicate directly with one another. The various components of the example patient management system 1400 illustrated herein are described below. The patient management system 1400 may be a single device or comprise multiple devices. In one embodiment, the patient management system 1400 is a single external computing device.

Data-generating devices 1402, 1404, and 1406 can be implantable devices or external devices that may provide one or more of the following functions with respect to a patient: (1) sensing, (2) data analysis, and (3) therapy. For example, in one embodiment, devices 1402, 1404, and 1406 are either implanted or external devices used to measure a variety of physiological, subjective, and environmental conditions of a patient using electrical, mechanical, and/or chemical means. In a variety of embodiments, at least one of the devices 1402, 1404, 1406 is an IMD.

The devices 1402, 1404, and 1406 can be configured to automatically gather data or can require manual intervention by the patient or another person. The devices 1402, 1404, and 1406 can be configured to store data related to the physiological and/or subjective measurements and/or transmit the data to the communication system 1410 using a variety of methods, described in detail below. Although three devices 1402, 1404, and 1406 are illustrated in the example embodiment shown, many more devices can be coupled to the patient management system. In one embodiment, each of the devices 1402, 1404 and 1406 is serving a different patient. In one embodiment, two or more devices are serving a single patient.

The devices 1402, 1404, and 1406 can be configured to analyze the measured data and act upon the analyzed data. For example, the devices 1402, 1404, and 1406 can be configured to modify therapy or provide an alarm based on the analysis of the data.

In one embodiment, devices 1402, 1404, and 1406 provide therapy. Therapy can be provided automatically or in response to an external communication. Devices 1402, 1404, and 1406 are programmable in that the characteristics of their sensing, therapy (e.g., duration and interval), or communication can be altered by communication between the devices 1402, 1404, and 1406 and other components of the patient management system 1400. Devices 1402, 1404, and 1406 can also perform self-checks or be interrogated by the communication system 1410 to verify that the devices are functioning properly. Examples of different embodiments of the devices 1402, 1404, and 1406 are provided herein.

Devices implanted within the body have the ability to sense and communicate as well as to provide therapy. Implantable devices can provide direct measurement of characteristics of the body, including, without limitation, electrical cardiac activity as described above, physical motion, temperature, heart rate, activity, blood pressure, breathing patterns, ejection fractions, blood viscosity, blood chemistry, blood glucose levels, and other patient-specific clinical physiological parameters, while minimizing the need for patient compliance. Derived measurements can also be determined from the implantable device sensors (e.g., a sleep sensor, functional capacity indicator, autonomic tone indicator, sleep quality indicator, cough indicator, anxiety indicator, and cardiovascular wellness indicator for calculating a quality of life indicator quantifying a patient's overall health and well-being).

Devices 1402, 1404, and 1406 can also be external devices, or devices that are not implanted in the human body, that are used to measure physiological data (e.g., a thermometer, sphygmomanometer, or external devices used to measure blood characteristics, body weight, physical strength, mental acuity, diet, heart characteristics, and relative geographic position).

The patient management system 1400 may also include one or more remote peripheral devices 1409 (e.g., cellular telephones, pagers, PDA devices, facsimiles, remote computers, printers, video and/or audio devices) that use wired or wireless technologies to communicate with the communication system 1410 and/or the host 1412.

The database module 1414 comprises memory for storing patient data. The patient data can include electrogram data, which comprises groups of device-identified beat locations for the electrogram data. This data may be received from a patient device, such as an implantable medical device, or it may be retrieved from another database 1480. The example database module 1414 includes a patient database 1440 and an episode database 1442, which are described further below. The patient database 1440 includes patient specific data, including data acquired by the devices 1402, 1404, and 1406, such as electrogram data, as well as a patient's medical records and historical information. The episode database 1442 has episode data regarding a plurality of different episodes generated from those of devices 1402, 1404, and 1406 that provide episode data. The episode database 1442 may also store data analyzed by the analysis module 1416.

Information can also be provided from an external source, such as external database 1480. For example, the external database 1480 could include external medical records maintained by a third party, such as drug prescription records maintained by a pharmacy, providing information regarding the type of drugs that have been prescribed for a patient or, in another example, authorization data from patient groups that have authorized users to view arrhythmia episode data. The external database 1480 may also store patient data that was previously acquired by an implantable or external medical device. One example of stored patient data on an external database 1480 is electrogram data.

The example analysis module 1416 includes a patient analysis module 1450 and a device analysis module 1452. Patient analysis module 1450 may utilize information collected by the patient management system 1400, as well as information for other relevant sources, to analyze data related to a patient and provide timely and predictive assessments of the patient's well-being. Device analysis module 1452 analyzes data from the devices 1402, 1404, and 1406 and external interface devices 1408 to predict and determine device issues or failures. For example, the device analysis module 1452 may analyze electrogram data to determine locations of heart beats on one or more channels using the multi-pass methods described above. The device analysis module 1452 can further compare device-identified beats and beat locations to beats and beat locations determined using the multi-pass method. The device analysis module 1452 can then perform comparisons to find the presence of noise, oversensing, and undersensing by the device, as described above.

The analysis module 1416 further includes an adjudication processor 1458, and episode processor 1460 and an overwrite processor 1462. In one embodiment, the adjudication processor is operatively connected to at least the episode database 1442 and is configured to receive as input episode data regarding one of the different episodes.

The episode processor 1460 performs processing of the adjudication database such as in order to provide reports, patient alerts, or programming recommendations. The overwrite processor 1462 can analyze data provided from the episode database 1442, and other portions of the patient management system 1400 to determine what particular portion of episode data for one of the episodes from the episode database should be displayed to a user. Overwrite processor 1462 can, through the delivery module 1418 described below, provide the means for graphically displaying a portion of data selected from arrhythmia episode data related to an episode of a patient, such as data generated by a data-generating device and stored in the episode database.

Overwrite processor 1462 also requests from a user any changes in the characterization data determined by the adjudication processor, and can articulate the request for user input characterizing an episode. The request may be a direct question to a user, a series of choices provided to the user, or simply a blank space on the user interface configured to accommodate the user input. The overwrite processor 1462 may also store the overwrite history for individual users.

One or more portions of the analysis module 1416, such as the adjudication processor 1458 and episode processor 1460 may be located remotely from other parts of the patient management system 1400. A microprocessor of a data-generating device may also serve as an adjudication processor in some embodiments.

Delivery module 1418 coordinates the delivery of reports, patient alerts or programming recommendations based on the analysis performed by the host 1412. For example, based on the data collected from the devices and analyzed by the host 1412, the delivery module 1418 can deliver information to the caregiver, user, or to the patient using, for example, a display provided on the external interface device 1408. A user interface device 1490 that is independent of a data-generating device may also be used to deliver information. The external interface device 1408 and user interface device 1490 are also configured, according to multiple embodiments, to display a report, alert, or programming recommendation, receive overwrite information from a user, and receive other data from the user. Displayed data, as described above, can be determined by the episode processor 1460, overwrite processor 1462 and delivery module 1418.

Figure 12:
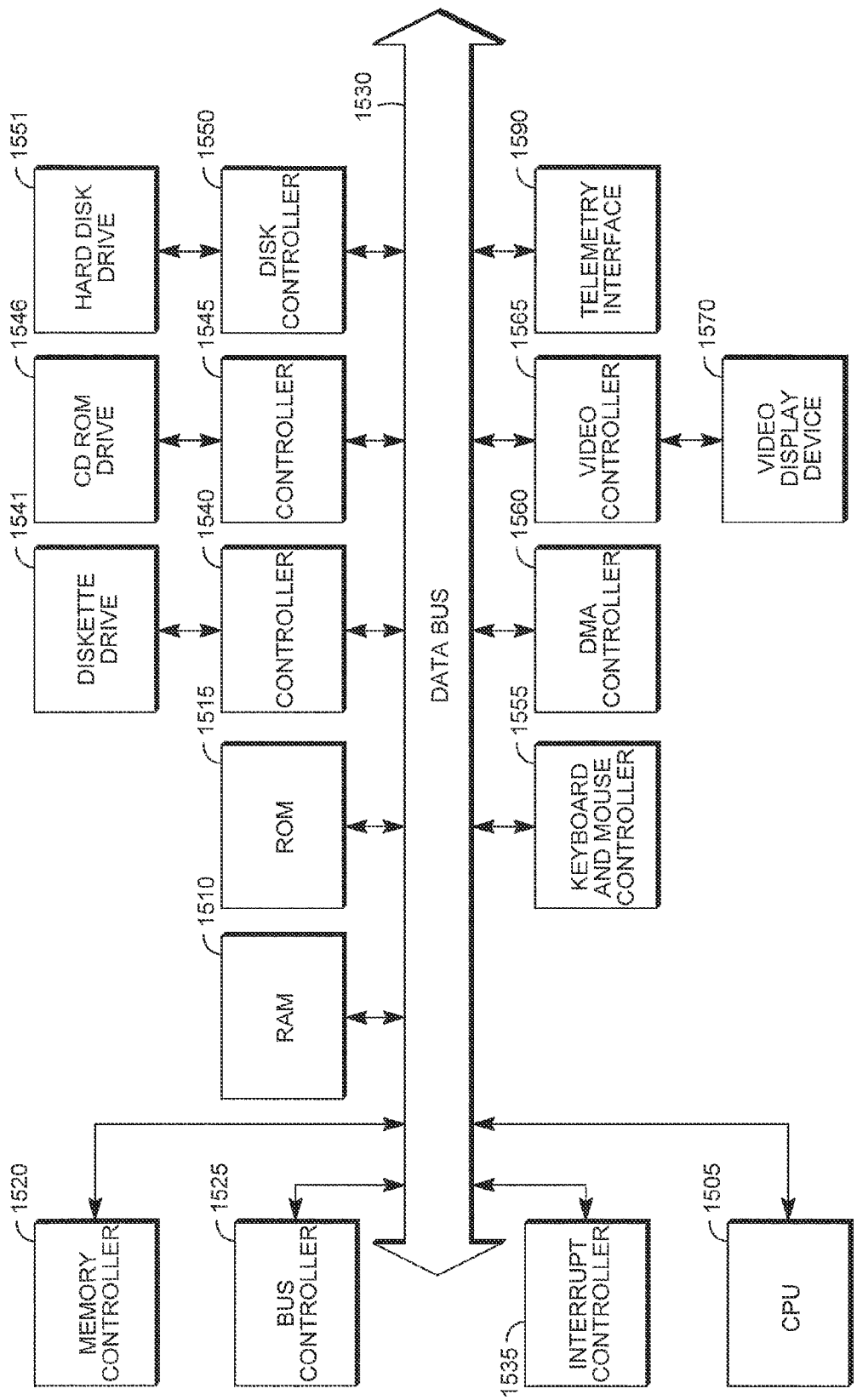
FIG. 12 depicts a schematic of various components consistent with some embodiments of the technology disclosed herein.

External interface devices 1408 to display information, such as programmer/recorder/monitors, can include components common to many computing devices. User interface devices 1490 to display and received information from users can also include components common to many computing devices. Referring now to FIG. 12, a diagram of various components is shown in accordance with some embodiments of the invention. However, it is not required that an external interface device have all of the components illustrated in FIG. 12.

In one embodiment, the external interface device includes a central processing unit (CPU) 1505 or processor, which may include a conventional microprocessor, random access memory (RAM) 1510 for temporary storage of information, and read only memory (ROM) 1515 for permanent storage of information. A memory controller 1520 is provided for controlling system RAM 1510. A bus controller 1525 is provided for controlling data bus 1530, and an interrupt controller 1535 is used for receiving and processing various interrupt signals from the other system components.

Mass storage can be provided by diskette drive 1541, which is connected to bus 1530 by controller 1540, CD-ROM drive 1546, which is connected to bus 1530 by controller 1545, and hard disk drive 1551, which is connected to bus 1530 by controller 1550. User input to the programmer system may be provided by a number of devices. For example, a keyboard and mouse can connected to bus 1530 by keyboard and mouse controller 1555. DMA controller 1560 is provided for performing direct memory access to system RAM 1510. A visual display is generated by a video controller 1565 or video output, which controls video display 1570. The external system can also include a telemetry interface 1590 or telemetry circuit which allows the external system to interface and exchange data with an implantable medical device. It will be appreciated that some embodiments may lack various elements illustrated in FIG. 12.

Figure 13:
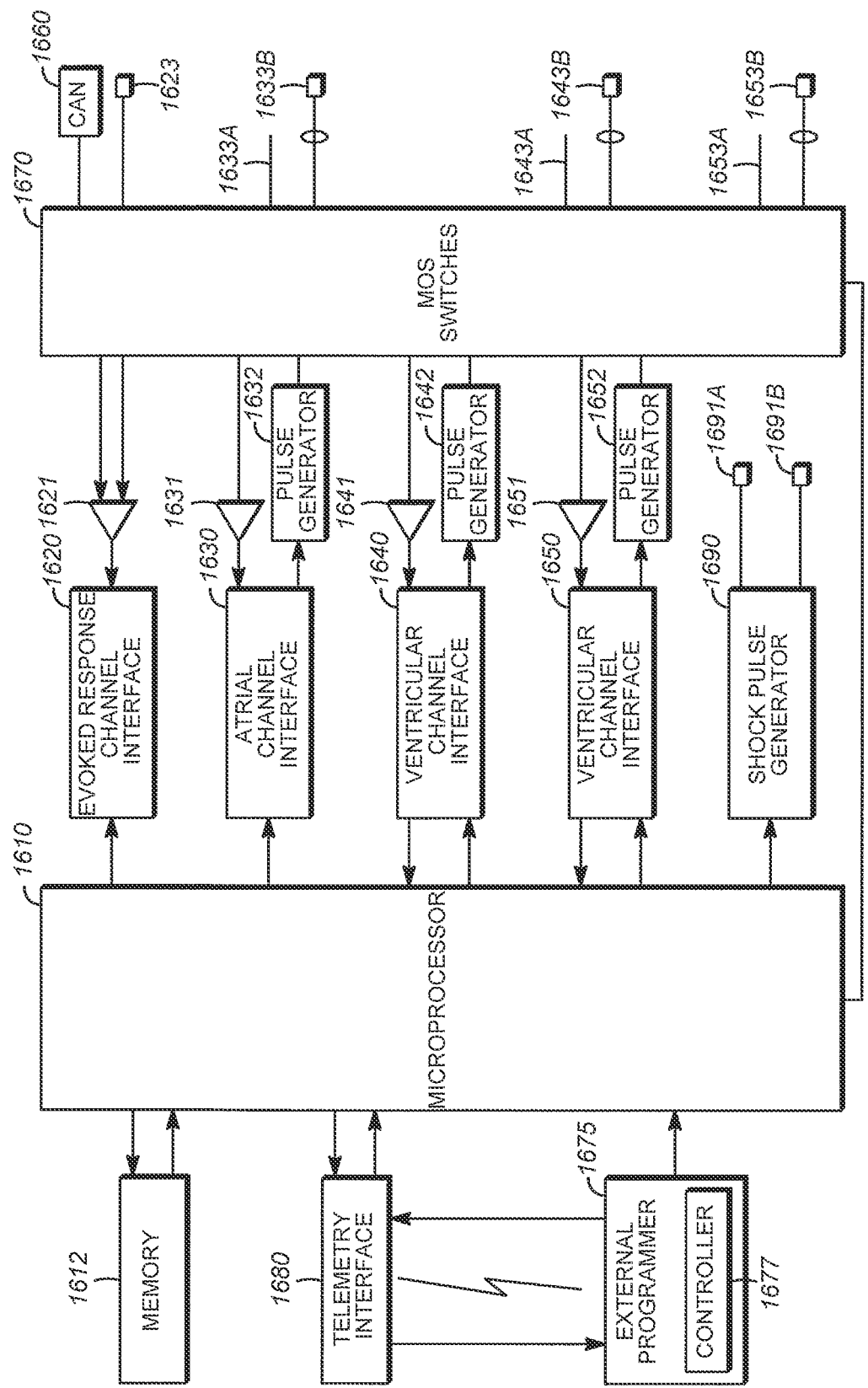
FIG. 13 depicts a schematic of some components of an exemplary implantable medical device.

Referring now to FIG. 13, some components of an exemplary IMD 1600 are schematically illustrated. The IMD 1600 can include a controller made up of a microprocessor 1610 communicating with a memory 1612, where the memory 1612 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the IMD 1600 in a number of programmed modes where a programmed mode defines how pacing pulses are output in response to sensed events and expiration of time intervals.

A telemetry interface 1680 is provided for communicating with an external programmer 1675. The external programmer is a computerized device with a controller 1677 that can interrogate the IMD 1600 and receive stored data as well as adjust the operating parameters of the pacemaker.

The IMD 1600 has an atrial sensing/pacing channel comprising ring electrode 1633A tip electrode 1633B sense amplifier 1631, pulse generator 1632, and an atrial channel interface 1630 which communicates bi-directionally with a port of microprocessor 1610. The device also has two ventricular sensing/pacing channels that similarly include ring electrodes 1643A and 1653A tip electrodes 1643B and 1653B sense amplifiers 1641 and 1651, pulse generators 1642 and 1652, and ventricular channel interfaces 1640 and 1650. For each channel, the electrodes are connected to the IMD 1600 by a lead and used for both sensing and pacing. A MOS switching network 1670 controlled by the microprocessor is used to switch the electrodes from the input of a sense amplifier to the output of a pulse generator. A shock channel is also provided comprising a shock pulse generator 1690 and shock electrodes 1691A and 1691B that enables the device to deliver a defibrillation shock to the heart when fibrillation or other tachyarrhythmia is detected. The IMD 1600 also has an evoked response sensing channel that comprises an evoked response channel interface 1620 and a sense amplifier 1621 that has its differential inputs connected to a unipolar electrode 1623 and to the device housing or can 1660 through the switching network 1670. The evoked response sensing channel may be used to verify that a pacing pulse has achieved capture of the heart in a conventional manner or, as explained below, used to record an evoked response electrogram.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 1610 controls the overall operation of the device in accordance with programmed instructions stored in memory. The sensing circuitry of the IMD 1600 generates atrial and ventricular sense signals when voltages sensed by the electrodes exceed a specified threshold. The controller then interprets sense signals from the sensing channels and controls the delivery of paces in accordance with a programmed pacing mode. The sensed signals from any of the sensing channels of the IMD 1600 in FIG. 13 can be digitized and recorded by the controller to constitute an electrogram that can either be transmitted via the telemetry link 1680 to the external programmer 1675 or stored for later transmission. The patient's cardiac activity may thus be observed in real-time or over a selected historical period.

The above-described method can be regularly initiated to analyze the implanted leads. Gathered data may be used as input for other device functionality, such as arrhythmia adjudication.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

We claim:

1. An external device for determining a lead-related condition associated with an implantable medical device (IMD) capable of being implanted in a patient:
   (a) a communication module configured to retrieve patient data from an IMD, wherein the patient data comprises at least episode data records each associated with an episode and a summary data record corresponding to one or more episodes;
   (b) a processing module configured to execute rapid sensing analysis comprising:
      (i) initiate periodic retrieval of a summary data record by the communication module from the IMD;
      (ii) apply an episode selection criteria to the summary data record to identify one or more episodes of interest,
      (iii) initiate retrieval from the IMD by the communication module of one or more episode data records associated with each episode of interest, and
      (iv) apply noise detection criteria to the one or more episode data records; and
   (c) a notification module configured to generate an alert if the noise detection criteria are satisfied.

2. The device of claim 1 wherein each summary data record of the one or more summary data records comprises a shock indicator indicating whether a shock was delivered by the IMD for a particular episode and the episode selection criteria excludes episodes during which a shock was delivered by the IMD.

3. The device of claim 1 wherein the processing module is configured to apply episode selection criteria to each summary data record comprising whether the episode was sustained and whether a shock was delivered.

4. The device of claim 3, wherein the processing module is configured to apply episode selection criteria to each summary data record comprising a therapy indicator indicating whether no therapy was attempted and whether anti-tachycardia pacing (ATP) was delivered by the IMD.

5. The device of claim 4, wherein the processing module is configured such that the episode selection criteria are satisfied if ATP was delivered during an episode.

6. The device of claim 3, wherein the processing module is configured such that the episode selection criteria are satisfied if an episode was sustained absent a delivered shock.

7. The device of claim 1 wherein the processing module is configured to apply noise detection criteria comprising first noise sub-criteria and second noise sub-criteria, and the noise detection criteria are satisfied if either the first or second noise sub-criteria are satisfied.

8. The device of claim 7 wherein:
   the first noise sub-criteria are satisfied if episodes with ATP delivered or episodes with a diverted shock are determined to contain noise based on applying a noise definition; and
   the second noise sub-criteria are satisfied if sustained episodes with no therapy attempted on two different days within a first time period are determined to contain noise based on applying the noise definition.

9. The device of claim 8 wherein the noise definition is satisfied if there are a threshold number of ventricular sensed beats that satisfy a first fast interval threshold.

10. The device of claim 9 wherein the threshold number of ventricular sensed beats is four.

11. The device of claim 1, wherein the processing module is further configured to execute an impedance spike analysis comprising:
   determination of an impedance median;
   identification of a number of impedance spikes relative to the median; and
   notification if the number of impedance spikes is more than a spike threshold.

12. The device of claim 11, further comprising a user interface to optionally select each of impedance spike analysis and rapid sensing analysis.

13. The device of claim 1 further comprising a memory configured to store retrieved summary data records, store retrieved episode data records, store outcomes of the application of noise detection criteria to retrieved episode data records and store alert notification records.

14. A method for lead analysis for an implanted medical device (IMD) comprising:
   (a) retrieving a summary data record associated with one or more episodes from an IMD through a communication module;
   (b) applying episode selection criteria to the summary data record by a processing module;
   (c) retrieving one or more episode data records from the IMD for one or more episodes for which the episode selection criteria was satisfied;
   (d) applying noise detection criteria to the episode data record; and
   (e) generating an alert if the noise detection criteria are satisfied.

15. The method of claim 14 wherein the summary data record includes a shock indicator indicating whether a shock was delivered by the IMD and wherein the episode selection criteria excludes episodes during which a shock was delivered by the IMD.

16. The method of claim 14 wherein applying episode selection criteria to the summary data record comprises determining whether the episode was sustained, whether shock was delivered, and whether anti-tachycardia pacing (ATP) was delivered by the IMD.

17. The method of claim 16, wherein the episode selection criteria are satisfied if ATP was delivered during an episode.

18. The method of claim 16, wherein the episode selection criteria are satisfied if an episode was sustained absent a delivered shock.

19. The method of claim 14, further comprising executing an impedance spike analysis comprising:
   determining an impedance median;
   identifying a number of impedance spikes relative to the median; and
   notifying if the number of impedance spikes is more than a spike threshold.

20. An external device for determining a lead-related condition associated with an implantable medical device (IMD) capable of being implanted in a patient:
(a) a communication module configured to retrieve patient data from an IMD, wherein the patient data comprises at least one or more episode data records each associated with an episode and a summary data record;
(b) a processing module configured to execute rapid sensing analysis comprising:
(i) initiate periodic retrieval of a summary data record by the communication module from the IMD;
(ii) apply an episode selection criteria to the retrieved summary data record to identify one or more episodes of interest,
(iii) initiate retrieval from the IMD by the communication module of one or more episode data records associated with each episode of interest, and
(iv) apply noise detection criteria to the one or more episode data record or records; and
(c) a notification module configured to generate an alert if the noise detection criteria are satisfied;
wherein each summary data record includes a shock indicator indicating whether a shock was delivered by the IMD for a particular episode and the episode selection criteria excludes episodes during which a shock was delivered by the IMD.

* * * * *